United States Patent
Roe et al.

(10) Patent No.: US 7,575,573 B1
(45) Date of Patent: Aug. 18, 2009

(54) ABSORBENT ARTICLE HAVING DRAWSTRING MEMBERS

(75) Inventors: Donald C. Roe, West Chester, OH (US); Connie L. Fisher, Cincinnati, OH (US); Carl L. Bergman, Loveland, OH (US); Gregg A. Flender, Quincy, MA (US)

(73) Assignee: The Procter & Gamble Company, Cincinnati, OH (US)

( * ) Notice: Subject to any disclaimer, the term of this patent is extended or adjusted under 35 U.S.C. 154(b) by 687 days.

(21) Appl. No.: 08/777,849

(22) Filed: Dec. 31, 1996

(51) Int. Cl.
*A61F 13/84* (2006.01)

(52) U.S. Cl. .......................... 604/385.29; 604/385.27; 604/385.3

(58) Field of Classification Search .............. 604/373, 604/385.1–386, 389–392, 393–396, 385.01, 604/397–402; 602/69, 71
See application file for complete search history.

(56) References Cited

U.S. PATENT DOCUMENTS

| | | | | | |
|---|---|---|---|---|---|
| 1,833,960 | A | * | 12/1931 | Alsep | 604/401 |
| 1,977,604 | A | * | 10/1934 | Alsop | 604/394 |
| 2,500,255 | A | * | 3/1950 | Lee | 604/392 |
| 2,926,666 | A | * | 3/1960 | Casper | 604/392 |
| 3,000,381 | A | * | 9/1961 | Mulhole et al. | 604/401 |
| 3,025,856 | A | * | 3/1962 | Burwell et al. | 604/394 |
| 3,039,466 | A | * | 6/1962 | Wilson | 604/394 |
| 3,417,751 | A | * | 12/1968 | Murdoch | 604/392 |
| 3,860,003 | A | * | 1/1975 | Buell | 604/385.25 |
| 4,081,301 | A | * | 3/1978 | Buell | 156/164 |
| 4,210,143 | A | * | 7/1980 | De Jonckheere | |
| 4,229,835 | A | * | 10/1980 | Shaw | 604/385.2 |
| 4,397,646 | A | * | 8/1983 | Daniels | 604/385.2 |
| 4,585,447 | A | | 4/1986 | Karami | |
| 4,695,278 | A | * | 9/1987 | Lawson | 604/385.27 |
| 4,699,621 | A | * | 10/1987 | Stevens et al. | 604/385.2 |
| 4,808,176 | A | * | 2/1989 | Kielpikowski | 604/386 |
| 4,816,025 | A | * | 3/1989 | Foreman | 604/385.27 |
| 4,850,988 | A | * | 7/1989 | Aledo et al. | 604/385.1 |
| 4,850,992 | A | * | 7/1989 | Amaral et al. | 604/385.1 |
| 4,883,481 | A | * | 11/1989 | Blanchard | 604/385.1 |

(Continued)

FOREIGN PATENT DOCUMENTS

CA          493293        *  6/1953   ................. 604/394

(Continued)

OTHER PUBLICATIONS

International Search Report dated Dec. 22, 1997.

*Primary Examiner*—Karin M Reichle
(74) *Attorney, Agent, or Firm*—Kevin C. Johnson; Jay A. Krebs; Charles R. Ware

(57) ABSTRACT

An absorbent article has a chassis assembly with a front region, a rear region, a crotch region disposed between the front and rear region, and a pair of longitudinal edges. A chamber is positioned adjacent to each longitudinal edge and extends from the front region to the rear region with each chamber being substantially enclosed. Drawstring members extend through each of the chambers and exit the chassis assembly from an opening in the rear region. A waist fit member extends across the rear region and is connected to a portion of the drawstring member. The drawstring members are substantially unattached to their respective chambers such that a more secure fit is provided about the legs and the waist of the wearer upon tensioning of the drawstring members.

12 Claims, 7 Drawing Sheets

U.S. PATENT DOCUMENTS

| | | | | |
|---|---|---|---|---|
| 4,932,950 A | * | 6/1990 | Johnson | 604/400 |
| 5,196,000 A | * | 3/1993 | Clear et al. | 604/385.29 |
| 5,370,634 A | * | 12/1994 | Ando et al. | 604/385.1 |
| 5,397,318 A | * | 3/1995 | Dreier | 604/385.19 |
| 5,454,803 A | * | 10/1995 | Sageser et al. | 604/386 |
| 5,540,796 A | * | 7/1996 | Fries | 156/164 |
| 5,554,144 A | * | 9/1996 | Roe et al. | 604/385.3 |
| 5,569,234 A | * | 10/1996 | Buell et al. | 604/396 |
| 6,315,764 B1 | * | 11/2001 | Faulks et al. | 604/385.24 |

FOREIGN PATENT DOCUMENTS

| | | | | | |
|---|---|---|---|---|---|
| CH | 282061 | * | 7/1952 | | 604/401 |
| DE | 1070779 | * | 12/1959 | | 604/397 |
| FR | 1117156 | * | 5/1956 | | 604/392 |
| FR | 1388974 | * | 1/1965 | | 604/386 |
| FR | 2 425 205 | | 12/1979 | | |
| FR | 2762507 A1 | * | 10/1998 | | |
| GB | 665724 | | 1/1952 | | |
| GB | 2 294 865 | | 5/1996 | | |

* cited by examiner

ABSORBENT ARTICLE HAVING DRAWSTRING MEMBERS

FIELD OF THE INVENTION

The present invention provides an absorbent article comprising drawstring members which provide enhanced fit of the absorbent article about a wearer. The drawstring members extend along the longitudinal edges of the absorbent article and are used to adjust the tension of the article about the legs and/or torso of a wearer.

BACKGROUND OF THE INVENTION

The need to provide better fit in an absorbent article to a wearer has been well documented. In articles such as diapers and incontinent devices, fastening systems, elastic leg cuffs, elastic waistbands and the like have been developed to provide closer, yet dynamic fit of an absorbent article to a user. For Example, U.S. Pat. No. 3,848,594 issued to Buell on Nov. 19, 1974 teaches tape fastening systems and U.S. Pat. No. 5,058,247 issued to Thomas on Oct. 22, 1991 teaches hook and loop fastening systems. The use of such fastening systems has provided diaperers with the freedom to adjust and re-adjust diapers, etc. about a wearer as needed.

In another example, U.S. Pat. No. 3,860,003 issued to Buell on Jan. 14, 1975 teaches leg cuffs that have been provided to elastically fit about a user's thighs. A user, especially a baby, may position itself in awkward positions necessitating dynamic fit of the diaper to a baby throughout these positions. Additionally, elastic waist bands have worked to provide dynamic, yet snug fit of a diaper about a wearer's waist.

All of these methods have worked well, however each has been structurally independent of one-another and out of the range of adjustment to a diaperer. Furthermore, a diaperer, until now, has been unable to tighten or loosen the elastic leg cuffs and waist bands because of their construction. The leg cuffs and waistbands mentioned above have been constructed such that they are out of reach and unalterable to a user. Manufacturers have set the tension in the leg cuffs and waistbands and then placed each out of the reach of a diaperer.

One opportunity to dynamically fit a diaper about a wearer is taught in U.K. Patent Application 2,001,236 (Raymond Pigneul). In this publication, Pigneul provides tapes, i.e., drawstrings, along each longitudinal side edge of the diaper. These tapes are housed within chambers or folds formed by the diaper chassis. The tapes are anchored at or near both end edges. At one end of the diaper, two openings exist whereby portions of the tapes forming loops protrude therefrom. Once the diaper is fitted on the wearer, the tapes are pulled about the diaper chassis by their loops. These loops are then secured to an anchoring element which is located on the backsheet or impermeable sheet of the chassis. Pigneul's tapes serve to not only create a tightness of his diaper to a user but also secure the diaper to a user without the use of any adhesives.

Therefore, it is an object of the invention herein to provide drawstrings for the purpose of establishing better fit of a diaper about a user's legs which can function independently of a fastening system.

It is an additional object of the invention herein to provide drawstrings for the purpose of establishing better fit of a diaper through a user's crotch region.

It is a further object of the invention herein to provide drawstrings which can be bonded only at one end of the diaper chassis.

Furthermore it is an object of the invention herein to provide adhesive and/or non-adhesive securing means on the drawstrings for securement of the drawstrings to the diaper chassis.

It is an additional object herein to provide securement of the drawstrings to the diaper chassis with or without a secondary fastening element, e.g., a receiving zone for tapes and/or hooks.

It is a further object herein to provide an embodiment whereby an elastic waist element is in structural and functional cooperation with the drawstrings.

These and other objects of the present invention will be more readily apparent when considered in reference to the following description and when taken in conjunction with the accompanying drawings.

SUMMARY OF THE INVENTION

Accordingly, the present invention provides an absorbent article comprising a chassis assembly having a topsheet, a backsheet having an inner surface and an outer surface joined to the topsheet, and an absorbent core located between the topsheet and the backsheet. The chassis assembly further comprises a front region, a crotch region adjacent to the front region on one side of the crotch region, a rear region adjacent to the crotch region on an opposing side of the crotch region, a longitudinal axis, a transverse axis, a pair of end edges, a pair of longitudinal edges, and a fastening means whereby the absorbent article is fastened about a wearer.

The chassis assembly comprises a pair of ear members that are positioned adjacent to the end edge in the rear region and extend outboard from the longitudinal edges of the absorbent chassis. Each ear member comprises a grasping region and a stretch region. At least one drawstring chamber is positioned adjacent to each longitudinal edge and extends from the ear member in the rear region to the front region. Each chamber is enclosed and a drawstring member extends through each of the chambers. Each drawstring member comprises a first end securely fastened to the chassis assembly within the ear members and a second end securely fastened to the chassis assembly within the front region. Preferably, the secured first ends of the drawstring members are secured within the grasping regions of each ear member.

In a preferred alternative of the above embodiment, a waist fit member of the same material types as the drawstring members is positioned adjacent to the end edge within the rear region. More specifically, the waist fit member is connected to each of the drawstring members and is more preferably connected to the first ends of each drawstring member.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
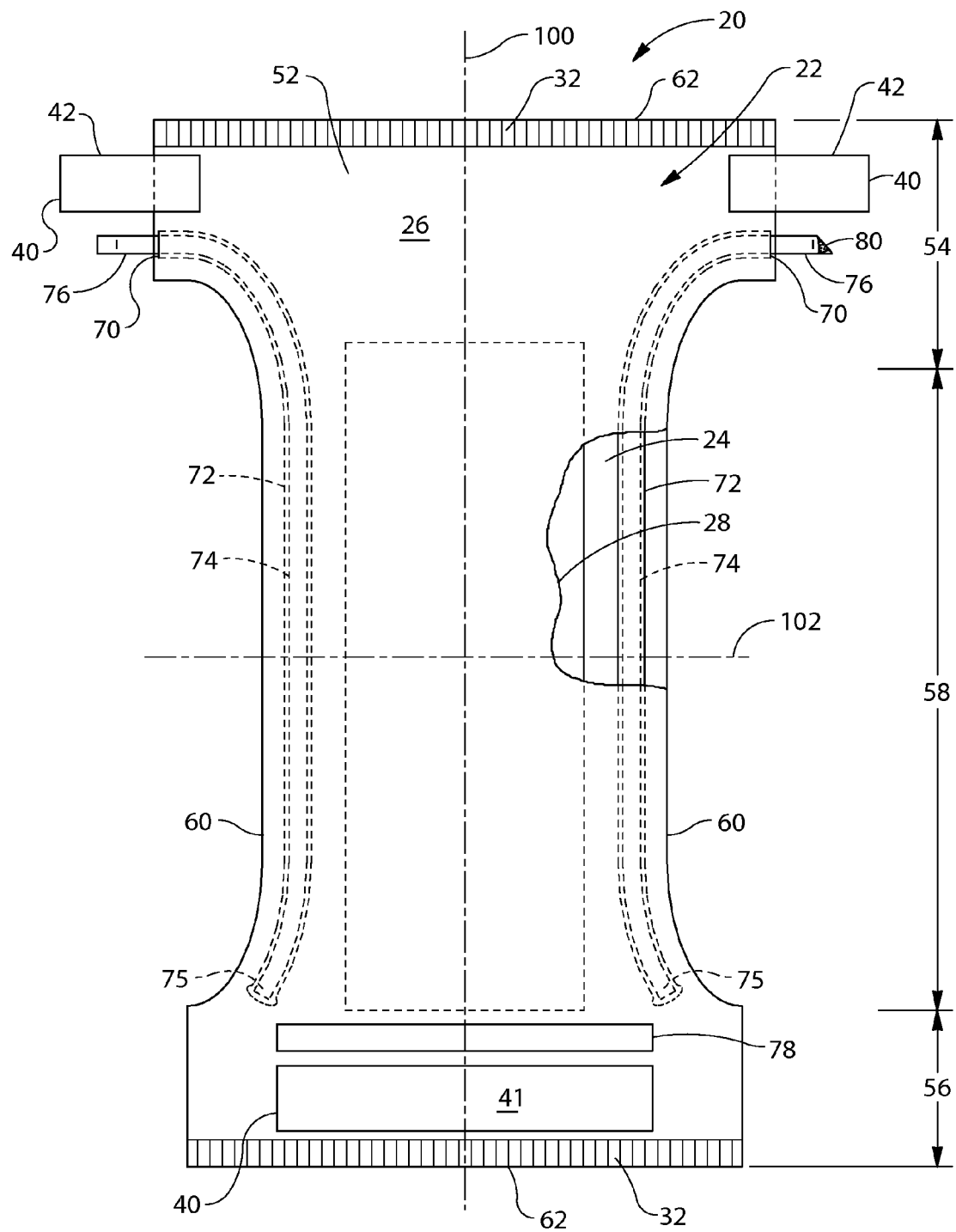
FIG. 1 is a plan view of an absorbent article of the present invention having portions cut-away to reveal underlying structure, the outer surface of the diaper facing the viewer.

The present invention provides an absorbent article comprising a chassis assembly having a topsheet, a backsheet having an inner surface and an outer surface joined to the topsheet, and an absorbent core located between the topsheet and the backsheet. The chassis assembly further comprises a front region, a crotch region adjacent to the front region on one side of the crotch region, a rear region adjacent to the crotch region on an opposing side of the crotch region, a longitudinal axis, a transverse axis, a pair of end edges, a pair of longitudinal edges, and a fastening means whereby the absorbent article is fastened about a wearer. A chamber is positioned adjacent to each longitudinal edge and extends from the front region to the rear region. Each chamber is substantially enclosed and has an end opening in the rear region. A drawstring member extends through each of the chambers, each drawstring member comprising a first end securely fastened to the chassis assembly within the front region and a second end extending outboard of the end opening in the rear region. In another embodiment herein, at least one drawstring and drawstring chamber are positioned substantially parallel to the longitudinal centerline and away from the longitudinal edges. This is to provide a fit means through a user's crotch region.

Preferably, the second ends of the drawstring members of each embodiment herein comprises at least one fastening element for securement of the tension applied in each drawstring member. The fastening elements are selected from the group consisting of hooks, loops, adhesive tape and cohesives. To compliment the fastening elements, the outer surface of the backsheet may comprise one or more receiving elements for connection with the fastening element. These receiving elements are selected from the group consisting of hooks, loops, and fastening surfaces.

For each embodiment of the present invention, the drawstring members may comprise at least one elastic component. Elastic components are selected from the group consisting of rubber elastics, synthetic elastics, elastomeric foams, structural elastic-like film webs and/or elastomeric films. The drawstring members may also comprise at least one inelastic component. Inelastic components are selected from the group consisting of nonwovens, films, laminates, foams, hi-loft nonwovens, string, twine, and/or braided rope.

In an alternative embodiment herein, the drawstring chambers are substantially enclosed and have their end openings in the front region rather than the rear region. Furthermore, the drawstring members are securely fastened at their first end within the rear region and their second ends extend outboard of the chamber opening in the front region.

In a particularly preferred embodiment of the present invention herein the absorbent article comprises a first surface and a second surface attached to the first surface. The attached first and second surfaces comprise a front region, a crotch region adjacent to the front region on one side of the crotch region, a rear region adjacent to the crotch region on an opposite side of the crotch region, a longitudinal axis, a transverse axis, a pair of end edges and a pair of longitudinal edges. The embodiment further comprises a pair of drawstring chambers. Each chamber is positioned adjacent to and extends along the longitudinal edge. Each chamber comprises a closed end in the front region and an open end in the rear region, and a drawstring member positioned within a chamber that extends within the chamber from the front region to the rear region. Each drawstring member has a secured first end in the front region and an unsecured second end extending through the opening in the rear region. The drawstring members each comprises a pull portion that extends out from the chamber openings. Additionally, the pull portions of the drawstring members preferably comprise fastening means thereon for securing the absorbent article about a wearer while simultaneously providing tension about the legs through the drawstring members.

An absorbent article, comprising: a chassis assembly comprising a topsheet, a backsheet joined to said topsheet, said backsheet having an inner surface and an outer surface, an absorbent core located between said topsheet and said backsheet, said chassis assembly having a front region, a rear region opposed to said front region, a crotch region located between said front region and said rear region, a longitudinal axis, a transverse axis, a pair of end edges, a pair of longitudinal edges, and fastening means whereby said absorbent article is fastened about a wearer; a chamber positioned adjacent each longitudinal edge and extending from said front region to said rear region, each said chamber being substantially enclosed and having an end opening in said rear region; a drawstring member extending through each of said chambers, each said drawstring member comprising a first end securely fastened to said chassis assembly within said front region and a second end extending outboard of said opening in said rear region; and a waist fit member positioned adjacent to said end edge within said rear region, said waist fit member being connected to each drawstring member. The absorbent article wherein said second ends of each said drawstring member comprises at least one fastening element. The absorbent article wherein said fastening elements are selected from the group consisting of hooks, loops, and adhesive tapes. The absorbent article wherein said outer surface of said backsheet comprises at least one receiving element for connection with said fastening elements. The absorbent article wherein said receiving elements are selected from the group consisting of hooks, loops, nonwovens and fastening surfaces. The absorbent article wherein said drawstring members comprise at least one elastic component. The absorbent article wherein each said elastic component is selected from the group consisting of rubber elastics, synthetic rubber elastics, elastomeric foams, structural elastic-like film webs and elastomeric films. The absorbent article wherein said drawstring members comprise at least one inelastic component. The absorbent article wherein each said elastic component is selected from the group consisting of nonwovens, films, laminates, foams, hi-loft nonwovens, string, twine, and braided rope. The absorbent article wherein each said chamber is formed by a portion of said topsheet. The absorbent article wherein each said chamber is formed by a portion of said backsheet. The absorbent article wherein each said chamber is formed by a portion of said topsheet and said backsheet.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a containment assembly or chassis 22 preferably comprising a liquid pervious topsheet 24, a liquid impervious backsheet 26 joined to the topsheet 24, and an absorbent core 28 positioned between the topsheet 24 and the backsheet 26. The diaper preferably further comprises elasticized waistbands 32; a fastening system 40 comprising a pair of first fastening members 42 and a second fastening member 41.

The diaper 20 is shown in FIG. 1 to have a chassis assembly 22 comprising an outer surface 52 (facing the viewer in FIG. 1), an inner surface 50 opposed to the outer surface 52, a front waist region 56, a rear waist region 54 longitudinally opposed to the front waist region 56, a crotch region 58 positioned between the front waist region 56 and the rear waist region 54, and a periphery which is defined by the outer perimeter or edges of the diaper 20 in which the longitudinal edges are designated 60 and the end edges are designated 62. The inner surface 50 (not shown) of the diaper 20 comprises that portion of the diaper 20 which faces toward the wearer's body during use (i.e., the inner surface 50 is generally formed by at least a portion of the topsheet 24 and other components joined to the topsheet 24). The outer surface 52 of the diaper 20 comprises that portion of the diaper 20 which faces away from the wearer's body during use (i.e., the outer surface 52 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The front waist region 56 and the rear waist region 54 extend from the end edges 62 of the periphery to the crotch region 58.

The diaper 20 also has two centerlines, a longitudinal centerline 100 and a transverse centerline 102. The term "longitudinal", as used herein, refers to a line, axis, or direction in the plane of the diaper 20 that is generally aligned with (e.g., approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves.)

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

FIG. 1 shows a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge", which issued to Kenneth B. Buell et al on Sep. 29, 1992; each of which is incorporated herein by reference.

Additionally, FIG. 1 discloses an embodiment wherein drawstring chambers 72 (or chambers) extend from the front waist region 56 to the rear waist region 54. These chambers 72 are positioned adjacent to the longitudinal edges 60 and preferably fitted between the topsheet 24 and backsheet 26. In one embodiment, the chambers 72 may comprise materials that are separate from the topsheet 24 and backsheet 26. That is, the chambers 72 may be separate members positioned between the topsheet 24 and backsheet 26. The chambers 72, as separate members herein, may be bonded or attached to the topsheet 24 and backsheet 26. Suitable bonding means herein may include adhesives and/or cohesive bonds known in the art, mechanical bonds, ultrasonic bonds, thermal bonds, and the like. In this embodiment, the chambers 72 should comprise materials that are compatible with the topsheet and backsheet: for example, nonwovens, polypropylene, polyethylene, and any other of the known fibers and synthetic materials used in like absorbent articles.

Figure 4A:
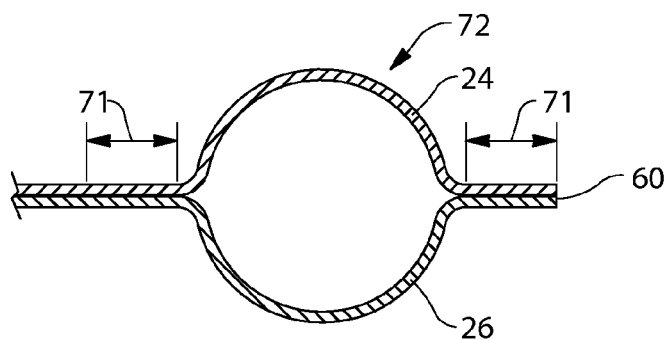
FIG. 4A is a cross-sectional view of a drawstring chamber of the present invention.
Figure 4B:
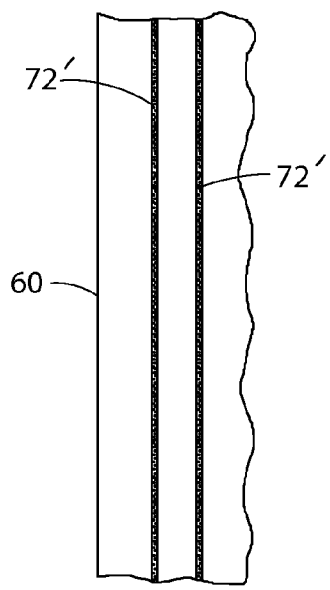
FIG. 4B is a plan view of the drawstring chamber in FIG. 4A.
Figure 4C:
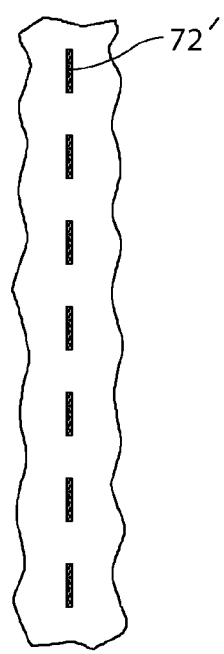
FIG. 4C is a plan view of an alternative embodiment of the lines of joining in FIG. 4B.
Figure 4D:
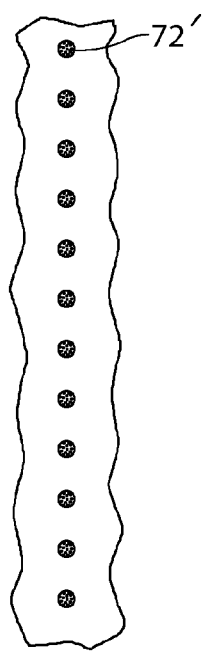
FIG. 4D is a plan view of an alternative embodiment of the lines of joining in FIG. 4B.
Figure 4E:
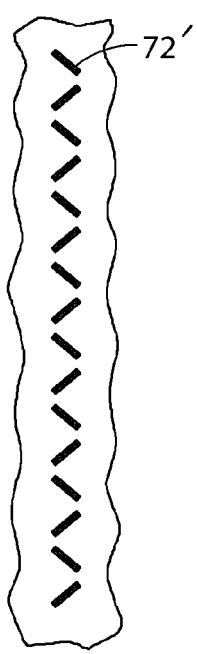
FIG. 4E is a plan view of an alternative embodiment of the lines of joining in FIG. 4B.

In one preferred embodiment, the chambers 72 are not separate members from the topsheet 24 and backsheet 26. Rather, the topsheet 24 and backsheet 26 together form the chambers 72 herein. This embodiment is preferred because it provides a savings in material usage and unit operations, i.e., fitting and attaching a chamber as a separate member to the diaper containment assembly 22. In this preferred embodiment, the chambers 72 are preferably formed from portions of the topsheet 24 and backsheet 26 brought together (e.g., folded over) and bonded in pre-determined locations to form an enclosure like that represented in FIGS. 4A and 4B. In FIG. 4A, a cross-section of a chamber 72 is shown in which portions of the topsheet 24 and backsheet 26 that are adjacent to a longitudinal edge 60 have been brought together along two points or regions of joining 71, which when the chamber is completed become two lines of joining 72'. This bonding can occur through any one of the known suitable adhesives used in disposable absorbent articles herein (i.e., for diapers and incontinent devices), but most preferably occurs through bonding (e.g., mechanical bonds, ultrasonic bonds, thermal bonds, and the like) the topsheet 24 and the backsheet 26 together along the lines of joining 72' shown in FIG. 4B. Lines of joining 72' may additionally comprise generally linear arrangements of spaced intermittent bonds as is shown in FIGS. 4C, 4D and 4E.

Figure 7:
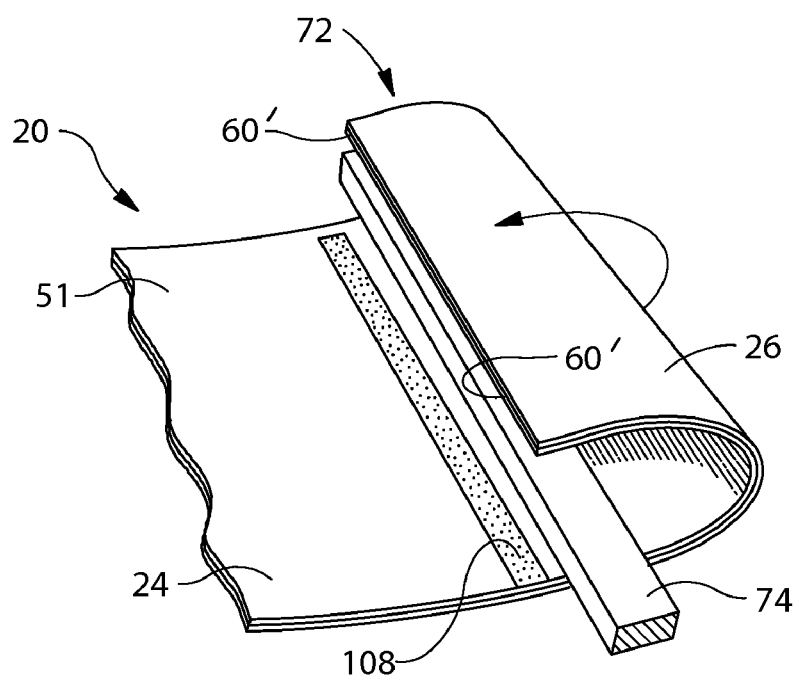
FIG. 7 discloses a partial view of portions of the backsheet and the topsheet in FIG. 1 being folded over to create a chamber that houses a drawstring member.

In an alternative embodiment of the chambers 72 herein, the chambers 72 may be formed from a portion of the backsheet 26 which has been folded over onto the topsheet 24, or a portion of the topsheet 24 which has been folded over onto backsheet 26. In another option, FIG. 7 discloses a partial view of portions of the backsheet 26 and the topsheet 24 being folded over to create a chamber 72 that houses a drawstring member 74. As is shown, the topsheet 24 and backsheet 26 portions are folded over and at least the end edge 60' is attached to the inner surface 51 of the topsheet 24 by a bonding means 108. The bonding means 108 can be one or more of the adhesive and/or cohesive bonds known in the art, mechanical bonds, ultrasonic bonds, thermal bonds, and the like.

In the embodiment shown in FIG. 1 drawstring members 74 are positioned within each chamber 72. Each enclosed chamber 72 has a chamber end opening 70 in the rear waist region 54. The drawstring members 74 have their first ends 75 securely fastened to the chassis 22 within the front waist region 56 and their second ends or pull portions 76 extending outboard of the openings 70 in the rear waist region 54. The drawstring members 74 have fastening elements 80 at the second ends 76. Additionally but not necessarily, the diaper 20 may include one or more receiving elements or members 78 on the outer surface 52 of the diaper 20, i.e., to receive the fastening elements 80.

The drawstring members 74 herein can be elastic and/or inelastic and are selected from the group of materials consisting of rubber elastics, synthetic rubber elastics, elastomeric foams, structural elastic-like film, elastomeric films, nonwovens, polyethylenes, polypropylenes, laminates, foams, highloft nonwovens, string, twine, and braided rope. Suitable structural elastic-like films are disclosed in U.S. Pat. No. 5,518,801 issued to Chappell, et al on May 21, 1996.

As is seen in FIG. 1, the drawstring members 74 are attached in the front waist region 56 at their first ends 75. From this point of attachment, the drawstring members 74 are substantially unattached throughout the chambers 72 and preferably the drawstring members 74, except for their attachment at their first ends 75, are not attached anywhere else within the chambers 72 and are therefore free to move within the confines of the chambers 72. The ability of the drawstring members 74 to move freely within the chambers 72 is important so that uniform tension is provided throughout the chambers 72 when the members 74 are pulled. Having uniform tension throughout the chambers 72 is important to ensure proper fit of a diaper 20 about a wearer. Unevenly tensioned chambers 72 may result in uneven or improper fit of a diaper 20 about the legs of a wearer.

Figure 2:
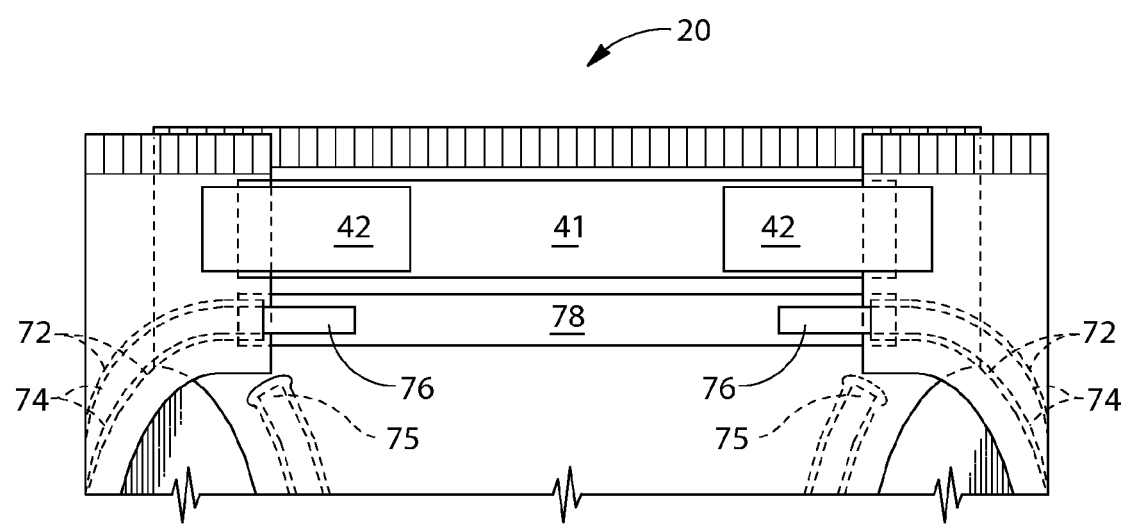
FIG. 2 is a partial view the absorbent article of FIG. 1 shown in a fastened condition.

FIG. 2 is a partial view that shows the diaper 20 of FIG. 1 in its wear or fastened position. Specifically, FIG. 2 shows the first fastening members or tabs 42 secured to the second fastening member 41 in the front waist region. Additionally, the pull portions 76 of the drawstring members 74 are shown extended beyond the chambers 72 and attached to the receiving member 78. Once the diaper 20 is fitted about a wearer, a diaperer can then adjust the fit about the legs of the wearer by pulling the pull portions 76 to tighten and/or loosen the fit as necessary. The term "diaperer" means herein one who fits a diaper, incontinent device, catamenial pad or other such absorbent articles about the wearer of one these articles. A diaperer and a wearer can be one in the same person. The pull portions 76 herein preferably comprise a fastening means that adheres to either the outer surface 52 of the backsheet 26 or to a receiving member 78. Suitable fastening means herein can be adhesives, hooks and/or loops. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; and the herein before referenced U.S. patent application Ser. No. 07/715,152; each of which is incorporated herein by reference. Exemplary fastening systems comprising mechanical fastening components (i.e., hooks and loops) are described in U.S. Pat. No. 5,058,247 entitled "Mechanical Fastening Prong" issued to Thomas Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; and U.S. Pat. No. 4,846,815 entitled "Disposable Diaper Having an Improved Fastening Device" issued to Scripps on Jul. 11, 1989. An example of a fastening system having combination mechanical/adhesive fasteners is described in U.S. Pat. No. 4,946,527 entitled "Pressure-Sensitive Adhesive Fastener and Method of Making Same" issued to Battrell on Aug. 7, 1990. Each of these patents are incorporated herein by reference.

It should be noted herein that the drawstring members 74 are secured to the diaper chassis such that the fastening elements 80 attached to the members 74 are joined to the front region 56. This is important as a wearer will best gain use of the tensioned drawstring members 74 when their tension is exerted through each region; i.e., the front region 56, the crotch region 58 and the rear region 54. Therefore, the best execution of the wear of the embodiments herein exists when the fastening elements 80 of the drawstrings members 74 are attached to the diaper chassis 22 within its front region 56.

Figure 3A:
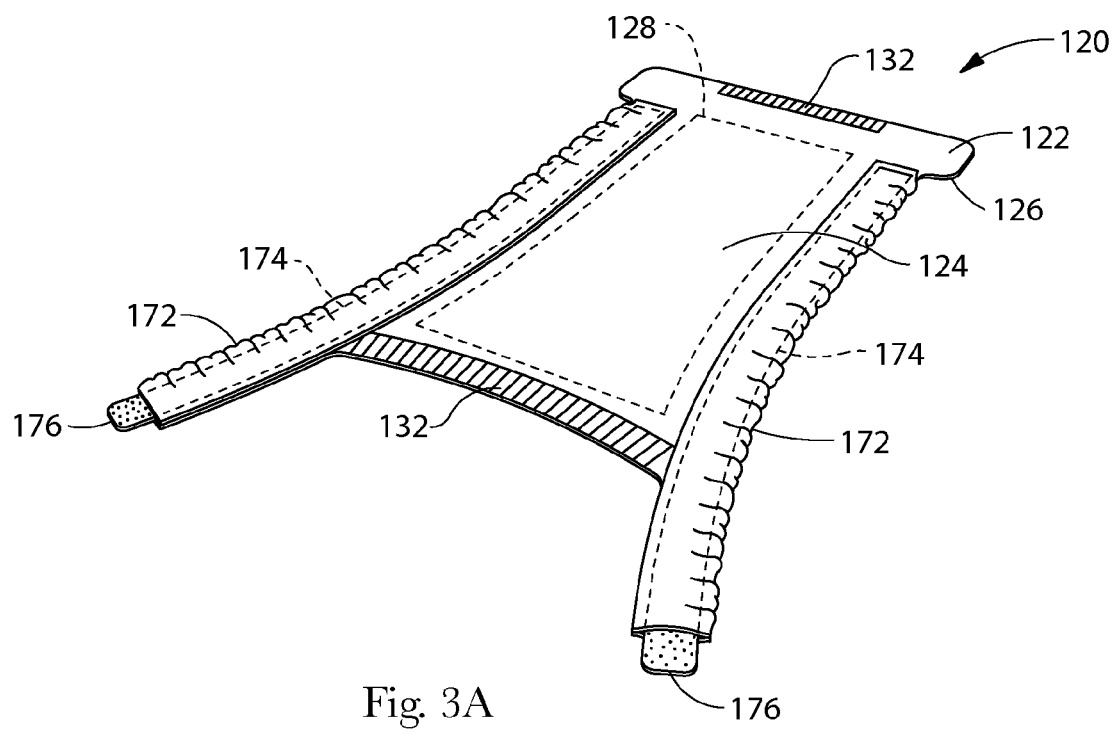
FIG. 3A is a perspective view of an alternative embodiment of an absorbent article of the present invention.
Figure 3B:
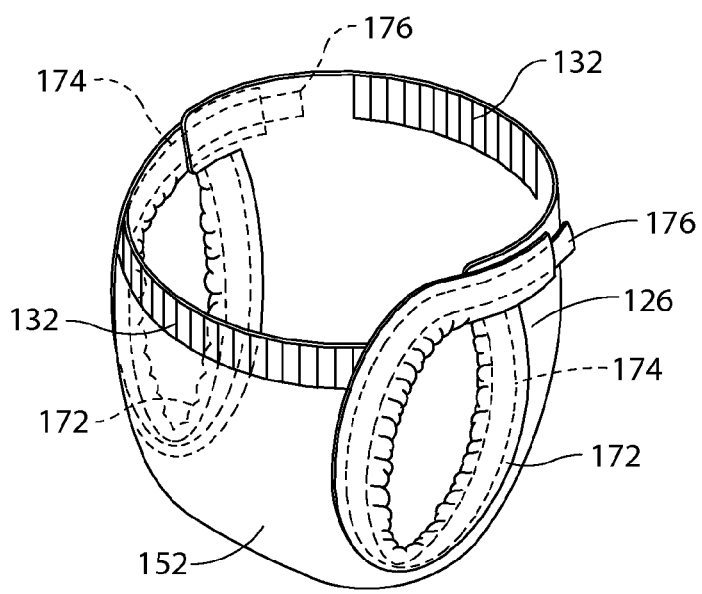
FIG. 3B is a perspective view of the absorbent article of FIG. 3A shown in a fastened condition.

FIGS. 3A and 3B disclose an alternative embodiment herein whereby the drawstring members operate not only to more securely fit a diaper about a wearer, but also serve as a portion of the fastening system. The fastening system herein is preferably a one element system, e.g., adhesive which attaches to a polyethylene backsheet or hooks which attach to a nonwoven backsheet. This would be critical where manufacturing priorities necessitate a single fastening system whereby only tapes are used to fasten the diaper chassis 22 to a wearer. FIG. 3A shows one embodiment possible for this use. Clearly, one skilled in the art could form any number of designs based upon the inventive concept herein.

FIG. 3A shows the diaper 120 in its flat-out uncontracted position with the topsheet 124 facing the viewer. This embodiment comprises an absorbent core 128 fitted between the topsheet 124 and the backsheet 126 (which faces away from the viewer in FIG. 3A). Preferably, the drawstring members 174 herein will be pretensioned such that the diaper chassis 122 will provide curvature compatible with the shape and contour of a wearer. Also preferably, the diaper 120 will comprise waistbands 132 that provide additional stretch about a wearer's torso. FIG. 3B shows the diaper 120 of FIG. 3A in it's fitted position. As shown, the pull portions 176 of the diaper 120 will extend out from their chambers 172 and fasten onto either the outer surface 152 of the backsheet 126 or onto a receiving member 178 (not shown). As in the embodiment in FIG. 1, the pull portions 176 may comprise any element from the group consisting of adhesives, hooks, and/or loops. Exemplary fastening systems herein are any of those disclosed for FIGS. 1 and 2.

Figure 5:
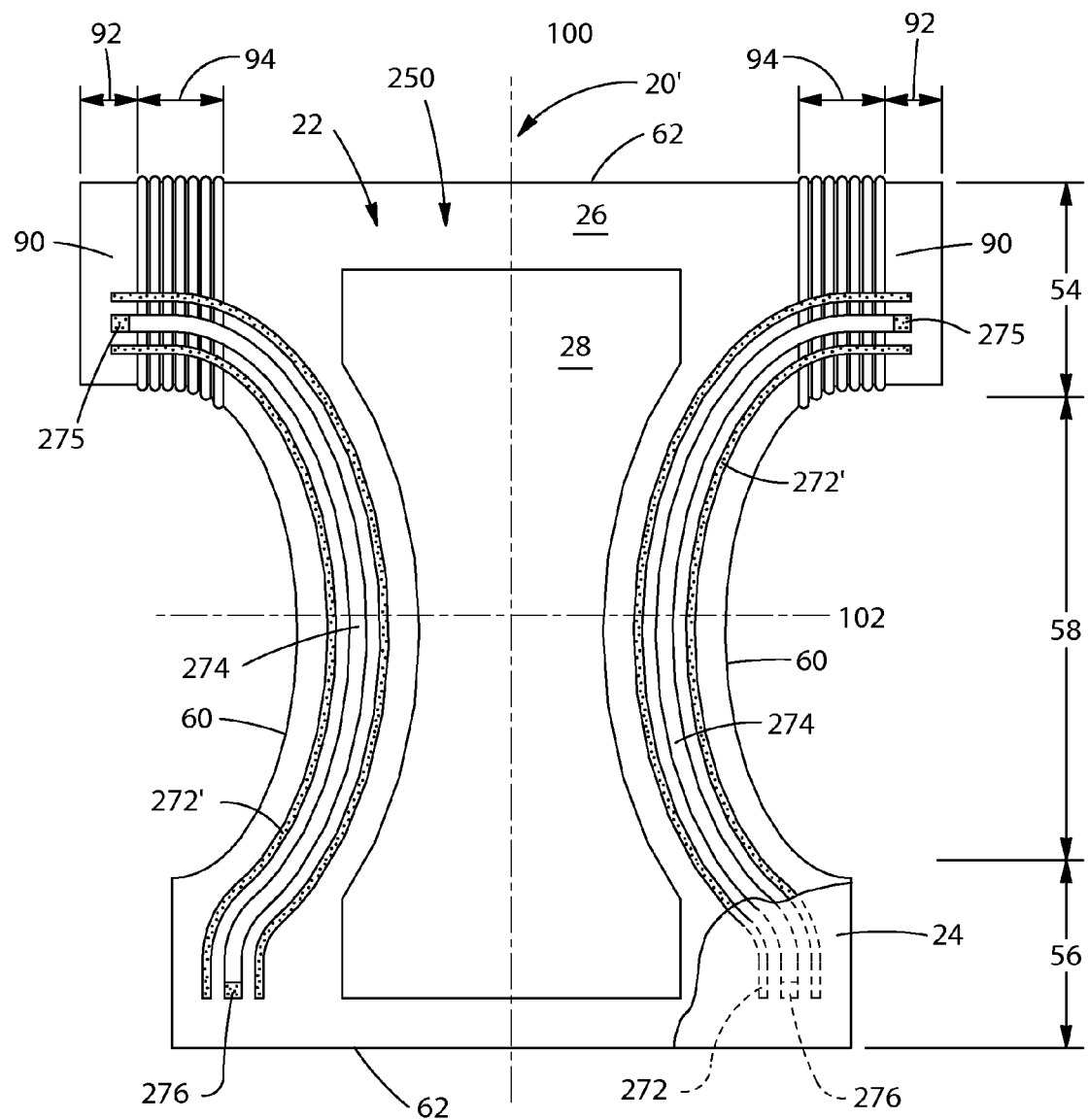
FIG. 5 is a plan view of an alternative embodiment of the absorbent article of the present invention having portions cut away to reveal underlying structure, the inner surface of the diaper facing the viewer.
Figure 6:
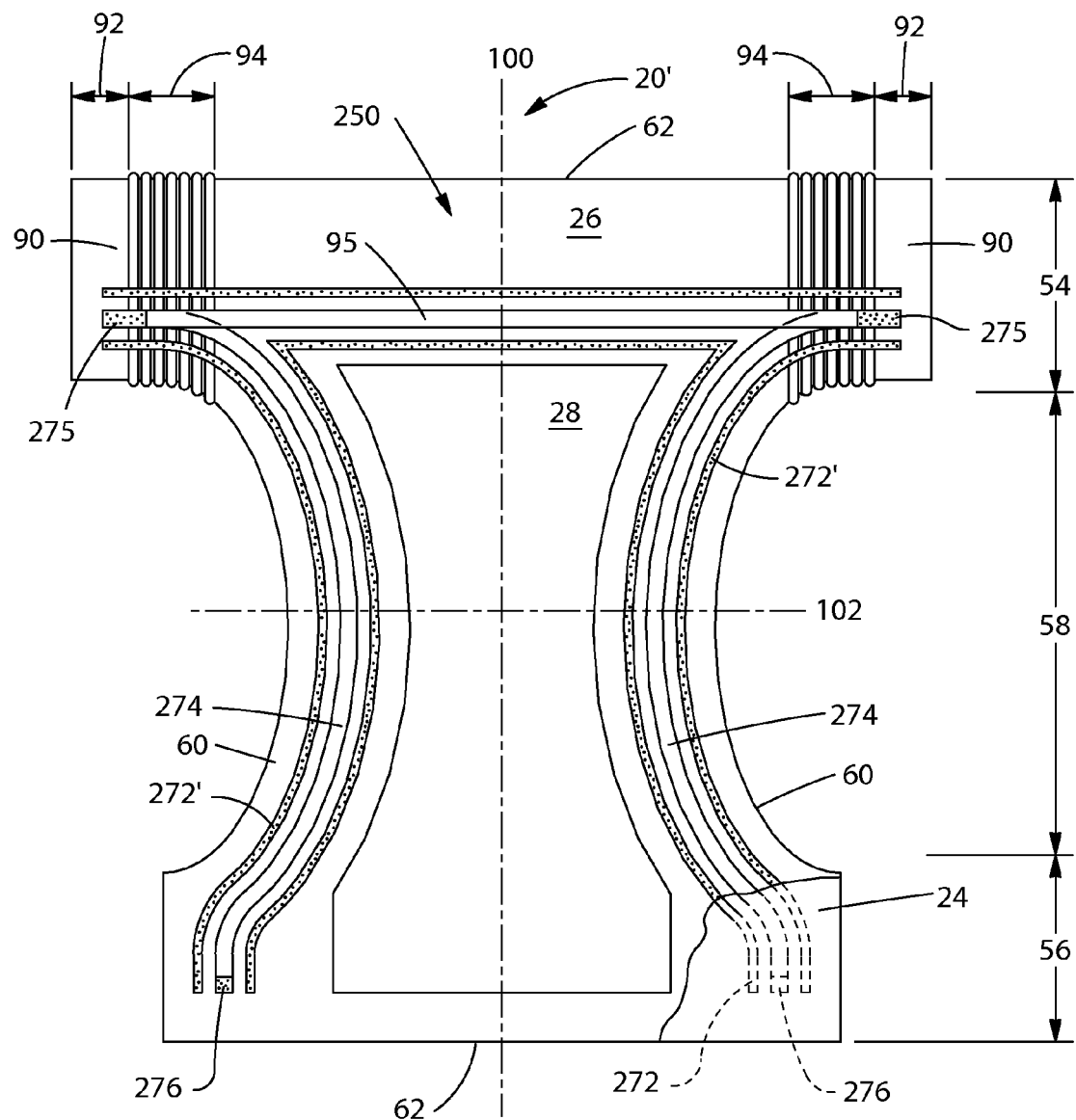
FIG. 6 is a plan view of an alternative embodiment of the absorbent article of the present invention having portions cut away to reveal underlying structure, the inner surface of the diaper facing the viewer.

In the embodiments shown in FIGS. 5 and 6, a diaper 20' comprises a chassis assembly 22 having a topsheet 24, a backsheet 26 having an inner surface 250 and an outer surface 252 (not shown) joined to the topsheet 24, and an absorbent core 28 located between the topsheet 24 and the backsheet 26. The chassis assembly 22 comprises a front waist region 56, a crotch region 58 adjacent to the front region 56 on one side of the crotch region 58, and a rear waist region 54 adjacent to the crotch region 58 on an opposite side of the crotch region 58. The chassis 22 further comprises a longitudinal axis 100, a transverse axis 102, a pair of end edges 62, and a pair of longitudinal edges 60. Ear members 90 are positioned in the rear region 54 and extend outboard from the longitudinal edges 60 of the absorbent chassis 22. Each ear member 90 comprises a grasping zone 92 and a stretch zone 94. A drawstring chamber 272 is positioned adjacent to each longitudinal edge 60 and extends from the ear members 90 in the front waist region 54 to the rear waist region 56. Each chamber 272 is enclosed. A drawstring member 274 extends through each of the chambers 272. Each drawstring member 274 comprises a first end 275 securely fastened to the chassis assembly 22 within the ear member 90 in the rear region 54 and a second end 276 securely fastened to the chassis assembly 22 within the front waist region 56.

In FIG. 5, the diaper 20' is shown with the topsheet 24 partially removed to reveal the underlying structure, i.e., the absorbent core 28 and backsheet 26. Also, the chamber covering is removed to show drawstring members 274. As shown, the first ends 275 of the drawstrings 274 are securely fastened within the ear members 90. In fact, the first ends 275 are preferably, but not necessarily, fastened within the grasping regions 92 of the ear members 90. This is preferable so that when a diaperer grasps the ear members 90 at the grasping regions 92, the drawstrings 74 will also preferably be directly grasped through the grasping regions 92 and therefore extended to fit about the wearer.

Generally, a diaper 20' of the above embodiment comprising ear members 90 is fitted about a wearer like a conventional diaper, i.e., bringing the front portion 56 through the wearer's legs. Next, a diaperer grasps the ear members 90 at the grasping zones 92 to secure the diaper 20' about a wearer. Preferably, the ear members 90 will comprise fastening tabs 42 (shown in FIG. 1) with which to fasten a diaper about a wearer. As the diaper 20' is secured to a wearer, i.e., the grasping portions 92 of the ear members 90 are pulled, the drawstrings 274 are put into tension to provide a more secure fit to a wearer about their legs and torso.

The drawstrings 74, 174 and 274 of each of the embodiments herein can be fitted to act alone as extensible leg cuffs or leg cuffs can be included as a separate attachment to the chassis' herein. A more detailed discussion of extensible leg cuffs is provided in latter portions of the specification.

FIG. 6 discloses a waist fit member 95 that is positioned adjacent to the end edge 62 within the rear waist region 54. The waist fit member 95 is connected to each drawstring member 274. The waist fit member may be housed within a chamber. Preferably, the waist fit member 95 is elastic to provide enhanced enclosure about a wearer's waist. Suitable elastics can be selected from the group consisting of rubber elastics, synthetic rubber elastics, elastomeric foams, structural elastic-like film webs and elastomeric films.

The diaper 20' of FIG. 6 also preferably comprises a fastening system 40 having first fastening members 42 preferably comprising fastening tabs and a second fastening member 41 that can attach to one-another to form a side closure which maintains the front waist region 54 (FIG. 1) and the rear waist region 56 (FIG. 1) in an overlapping configuration such that lateral tensions are maintained around the circumference of the diaper to maintain the diaper on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; and the herein before referenced U.S. patent application Ser. No. 07/715,152; each of which is incorporated herein by reference.

Examples of suitable adhesive tape tab fastening systems are disclosed in U.S. Pat. No. 3,848,594 issued to Buell on Nov. 19, 1974; and U.S. Pat. No. 4,662,875 issued to Hirotsu and Robertson on May 5, 1987; each of which are incorporated herein by reference. Examples of other closure systems, including mechanical closure systems, useful in the present invention, are disclosed in U.S. Pat. No. 4,869,724 issued to Scripps on Sep. 26, 1989; U.S. Pat. No. 4,848,815 issued to Scripps on Jul. 11, 1989; and the two-point fastening system described in U.S. Pat. No. 5,242,436 issued to Weil, Buell, Clear, and Falcone on Sep. 7, 1993; each of which are incorporated herein by reference. When a two-point fastening system is used, the waist closure members of the waist closure system are preferably longitudinally aligned with the extensible front waist feature 32 and laterally aligned with the elastic strands of the extensible leg cuff 30 to provide an effective closure about both the legs and the waist. As shown throughout the disclosure, the diaper 20 may be provided with a pair of fastening tabs 42 that allow the side panels to be first joined together. The diaperer then brings the chassis assembly 22 between the legs of the wearer and joins the assembly 22 to the outer layer of the waist feature. Such a configuration and securing method is more fully described in the above-referenced U.S. application Ser. No. 08/044,562(New, et al.)

The fastening system can comprise any attachment means known in the art including pressure sensitive adhesives, cohesive materials, mechanical fasteners such as hook and loop type fasteners, or any combination of these or any other attachment means known in the art. Exemplary adhesive tape tab fastening systems are disclosed in U.S. Pat. No. 3,848,594 entitled "Tape Fastening System for Disposable Diaper" issued to Buell on Nov. 19, 1974; and U.S. Pat. No. 4,662,875 entitled "Absorbent Article" issued to Hirotsu and Robertson on May 5, 1987. Exemplary fastening systems comprising mechanical fastening components are described in U.S. Pat. No. 5,058,247 entitled "Mechanical Fastening Prong" issued to Thomas Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; and U.S. Pat. No. 4,846,815 entitled "Disposable Diaper Having an Improved Fastening Device" issued to Scripps on Jul. 11, 1989. An example of a fastening system having combination mechanical/adhesive fasteners is described in U.S. Pat. No. 4,946,527 entitled "Pressure-Sensitive Adhesive Fastener and Method of Making Same" issued to Battrell on Aug. 7, 1990. Each of these patents are incorporated herein by reference.

As discussed, one embodiment of the present invention comprises a hook fastening material preferably comprising a base and a plurality of engaging elements extending from the base. The hook fastening material is intended to engage fibrous elements of a loop fastening material so as to provide a secure fastening device. Thus, the hook fastening material may be manufactured from a wide range of materials. Further, the engaging elements may have any shape such as hooks, "T's", "mushrooms" or any other shape as are well known in the art. Suitable materials include nylon, polyester, polypropylene, or any combination of these materials. Examples of preferred hook fastening materials are available from Aplix of Charlotte, N.C. under the trade designation 960, 957 and 942. Other preferred hook fastening materials are available from the Minnesota Mining and Manufacturing Company of St. Paul, Minn. under the trade designations CS200, CS300, MC5 and MC6. Another preferred hook fastening material is described in U.S. Pat. No. 5,058,247 entitled "Mechanical Fastening Prong" issued to Thomas Oct. 22, 1991 which is incorporated herein by reference.

In the fastening systems 40 of the embodiments herein, the second fastening member preferably comprises a fastening element engageable with the hook member. Thus, the second fastening member may be manufactured from a wide range of materials and configurations capable of securely engaging the hook member. For example, the second fastening member may comprise identical complementary elements or distinct complementary elements. As used herein, the term "identical complementary elements" is used to define mechanical fastening systems wherein the engaging elements of the hook member and the second fastening member comprise the same configuration or structure that are interlocking. Examples of such systems are described in Brown et al. U.S. Pat. No. 4,322,875 entitled "Two Strip Materials Used For Forming Fasteners" issued on Apr. 16, 1982 and Kellenberger et al. U.S. Pat. No. 4,701,179 entitled "Fixed Position Fasteners For Disposable Absorbent Garments" issued on Oct. 20, 1987. The term "distinct complementary elements" is used herein to designate a system wherein the hook member is different from the second fastening member but is engageable therewith.

In one preferred embodiment, the second fastening component comprises a plurality of fiber elements, such as a loop fastening material, that engage the engaging elements of the hook component. The loop fastening material may be manufactured from a wide range of materials to provide fiber elements, preferably being loops. Suitable materials include woven materials, nonwovens, nylons, polyesters, polypropylenes, or any combination of these materials. One suitable loop fastening material is a nonwoven available from Minnesota Mining and Manufacturing Company, St. Paul, Minn. under the trade designation EBL. A preferred loop fastening material comprises a number of shaped engaging elements projecting from a woven backing such as the commercially available material designated Guilford 18904 available from Guilford Mills of Greensboro, N.C. Other suitable loop components are available from the Minnesota Mining and Manufacturing Company of St. Paul, Minn. under the trade designation EBL. An inexpensive loop fastening material and a method of making the same is described in U.S. Pat. No. 5,032,122, entitled "Loop Fastening Material For Fastening Device and Method of Making Same" issued to Noel et al., Jul. 16, 1991, which application is incorporated herein by reference. Another suitable loop material is described in U.S. Pat. No. 5,326,612 entitled "Nonwoven Female Component for Refastenable Fastening Device and Method of Making the Same" issued to David J. K. Goulait on Jul. 5, 1994, which is hereby incorporated by reference herein. Yet other suitable second fastening components are described in co-pending U.S. patent application Ser. No. 08/254,814 entitled "Nonwoven Female Component For Refastenable Fastening Device and Method of Making the Same" filed Jun. 6, 1994 in the names of Patrick Jay Allen et al.; U.S. patent Ser. No. 08/287,571 entitled "Nonwoven Female Component For Refastenable Fastening Device" filed Aug. 9, 1994 in the names of Willie F. King et al.; and U.S. patent Ser. No. 08/374,269 entitled "Female Component For Refastenable Fastening Device" filed Jan. 18, 1995 in the names of Carl L. Bergman et al.

The fastening elements may be disposed on either the outer surface or the inner surface of the diaper 20. In a preferred embodiment, however, the fastening elements are disposed on the diaper 20 such that the fasteners do not irritate the wearer's skin. In addition, the fastening elements may either be a discrete separate element affixed to the diaper 20 or a unitary piece of material that is neither divided nor discontinuous with an element of the diaper 20 such as the topsheet 24 or the backsheet 26. While the fastening elements can assume varying sizes and shapes, they preferably comprise one or more separate patches of material joined to the diaper 20 to allow for the best fit for a broad range of wearers.

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to an intermediate member(s) which in turn is affixed to the other element. In a preferred embodiment of the present invention, the topsheet 24 and the backsheet 26 are joined directly to each other in the diaper periphery and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 inches). Preferably, the topsheet has a basis weight from about 18 to about 25 grams per square meter. A suitable topsheet is manufactured by Veratec, Inc., a Division of International Paper Company, of Walpole, Mass. under the designation P-8. There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like.

A suitable topsheet comprises an apertured formed film. Apertured formed films are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The apertured topsheet for the present invention is the formed film described in one or more of the above patents and marketed on sanitary napkins by The Procter & Gamble Company of Cincinnati, Ohio as "DRI-WEAVE".

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, heat/pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). The backsheet preferably comprises a polyethylene blend film of about 0.025 mm (1.0 mil) as is manufactured by Tredegar Corporation of Terre Haute, Ind. and marketed as P8863.

The absorbent core 28 may be any absorbent means which is capable of absorbing and retaining liquids such as urine and other certain body exudates. The absorbent core 28 has a garment surface, a body surface, side edges, and waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulose fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults. FIG. 1 shows a preferred embodiment of the diaper 20 having a rectangular-shape absorbent core.

An absorbent structure useful as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; U.S. Pat. No. 4,888,231 entitled "Absorbent Core Having A Dusting Layer" issued to Angstadt on Dec. 19, 1989; U.S. Pat. No. 5,147,345 entitled "High Efficiency Absorbent Articles For Incontinence Management", issued to Young, LaVon & Taylor on Sep. 15, 1992; U.S. Pat. No. 5,102,597 entitled "Porous, Absorbent, Polymeric Macrostructures and Methods Of Making the Same", issued to Roe, Lahrman and Berg on Apr. 7, 1992; and U.S. Pat. No. 4,834,735, entitled "High Density Absorbent Members Having Lower Density and Lower Basis Weight Acquisition Zones", issued to Alemany and Berg on May 30, 1989; also describe absorbent structures that are useful in the present invention. The absorbent core 28 is preferably the dual-layer absorbent structure described in U.S. Pat. No. 5,234,423 entitled "Absorbent Article With Elastic Waist Feature and Enhanced Absorbency", issued to Alemany and Clear on Aug. 10, 1993. Each of these patents are incorporated herein by reference.

In a preferred embodiment of the present invention, an acquisition layer(s) may be positioned between the topsheet 24 and the absorbent core 28 and joined to the absorbent core 28. The acquisition layer may serve several functions including improving wicking of exudates over and into the absorbent core. There are several reasons why the improved wicking of exudates is important, including providing a more even distribution of the exudates throughout the absorbent core 28 and allowing the absorbent structure to be made relatively thin. The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton is or cellulose; blends of such fibers; or any equivalent materials or combinations of materials. Examples of absorbent structures disclosed herein having an acquisition layer and a topsheet are more fully described in U.S. Pat. No. 4,950,264 issued to Osborn and U.S. patent application Ser. No. 07/944,764, "Absorbent Article Having Fused Layers", filed Oct. 7, 1992, in the names of Cree, et al. Each of these references are incorporated herein by reference. In a preferred embodiment, the acquisition layer may be joined with the topsheet 24 and separate from the inserted absorbent material or absorbent core 28 by any of the conventional means for joining webs together, most preferably by fusion bonds as is more fully described in the above-referenced Cree application.

For all purposes herein, the topsheet 124, backsheet 126, absorbent core 128, and acquisition layers of the FIGS. 3A and 3B comprise the same materials and are made in the same fashion as those discussed for topsheets 24, backsheets 26, absorbent cores 28, and acquisition layers of all other embodiments herein.

The diapers 20 and 120 may preferably further comprises extensible leg cuffs for providing improved containment of liquids and other body exudates. Each extensible leg cuff may comprise several different embodiments for reducing the leakage of body exudates in the leg regions. (The leg cuff can be and is sometimes also referred to as leg bands, leg flaps, barrier cuffs, or elastic cuffs.) U.S. Pat. No. 3,860,003 entitled "Contractable Side Portions For a Disposable Diaper" issued to Buell on Jan. 14, 1975, describes a disposable diaper which provides a contractible leg opening having a leg flap and one or more elastic members to provide an elasticized leg cuff (gasketing cuff). U.S. Pat. No. 4,909,803 entitled "Disposable Absorbent Article Having Elasticized Flaps" issued to Aziz & Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. U.S. Pat. No. 5,032,120 entitled "Disposable Absorbent Article Having Improved Leg Cuffs" issued to Freeland & Allen on Jul. 16, 1991, discloses an absorbent article having leg cuffs having a relatively low ultimate contact force at relatively high elongation's accomplished, for example, by low contact force differential material. U.S. Pat. No. 5,087,255 entitled "Absorbent Article Having Inflected Barrier Cuffs" issued to Sims on Feb. 11, 1992, discloses an absorbent article having inflected barrier cuffs with the distal edge positioned outboard of the proximal edge in one waist region and inboard in the other to provide better fit about the hips/buttocks. Each of these patents are incorporated herein by reference.

The diapers 20 and 120 further comprise extensible waist features that provide improved fit and containment. The extensible waist features at least extend longitudinally outwardly from a containment assembly, preferably a respective waist edge of the absorbent core, and generally form at least a portion of the end edge of the diaper 20 or 120. While a disposable diaper of the present invention is constructed with an extensible waist feature disposed in each waist region (an elastic waist feature and an extensible front waist feature), the discussion will focus on diapers having different configurations for each extensible waist feature. At a minimum, it is preferred that the diaper at least have one of the extensible waist features constructed according to the present invention, more preferably at least the elastic waist feature. The waist features can be constructed as a separate element joined to the containment assembly or as an extension of other elements of the diaper (i.e., unitary). The waist features will be described with respect to preferred embodiments in which certain portions or panels comprise an extension of other elements of the diaper such as the backsheet, the topsheet, or both, and other portions or panels comprise a separate element joined to other portions or panels of the waist feature or other panels of the diaper.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a chassis assembly having a front region, a rear region opposed to said front region, a crotch region located between said front region and said rear region, a pair of end edges, a first longitudinal edge, and a second longitudinal edge opposed to said first longitudinal edge, said chassis assembly further comprising:

a topsheet, a backsheet joined to said topsheet; an absorbent core located between said topsheet and said backsheet; a first ear member disposed in said rear region of said chassis assembly, said first ear member comprising a grasping region, a stretch region between said grasping region and said absorbent core, and a fastening element positioned on said grasping region; a second car member disposed in said rear region of said chassis assembly, said second ear member comprising a second grasping region, a second stretch region between said second grasping region and said absorbent core, and a second fastening element positioned on said second grasping region; a first chamber positioned adjacent said first longitudinal edge in said crotch region and extending from said first ear member within said grasping region to said front region; a second chamber positioned adjacent said second longitudinal edge in said crotch region and extending from said grasping region of said second car member to said front region; a first substantially inelastic drawstring member extending from said first ear member to said front region through said first chamber, said first drawstring member comprising a first end second to said first ear member, a second end secured to said chassis assembly in said front region, wherein said first drawstring member is not directly attached to said chassis assembly in said first chamber between said first end and said second end such that when said grasping region of said first ear member is pulled, said first drawstring member is put into tension to provide a more secure fit; and a second substantially inelastic drawstring member extending from said second ear member to said front region through said second chamber, said second drawstring member comprising a first end secured to said second ear member and a second end secured to said chassis assembly in said front region, wherein said second drawstring member is not directly attached to said chassis assembly in said second chamber between said first end and said second end such that when said grasping region of said second ear member is pulled, said second drawstring member is put into tension to provide a more secure fit, wherein the absorbent article further comprises an elastic waist fit member disposed in said rear region, said waist fit member extending from said first ear member to said second ear member, said first drawstring member having a portion directly connected to and overlapping with said waist fit member in the rear region, and said second drawstring member having a portion directly connected to and overlapping with said waist fit member in the rear region such that when said grasping portion of said first ear member is pulled, said waist fit member is put into tension to provide a more secure fit.

2. The absorbent article as recited in claim 1 wherein the first ends of the first and second drawstrings are wholly aligned with the rear region.

3. The absorbent article as recited in claim 2 wherein the second ends of the first and second drawstrings are wholly aligned with the front region.

4. The absorbent article as recited in claim 1 wherein said first ends of the first and second drawstrings comprise the portion connected to and overlapping with said waist fit member.

5. The absorbent article as recited in claim 1 wherein said waist fit member comprises a material selected from the group consisting of a rubber elastic, a synthetic rubber elastic, an elastomeric foam, a film web, and an elastomeric film.

6. The absorbent article of claim 1 wherein each said drawstring members comprise a material selected from the group consisting of nonwovens, films, laminates, foams, highloft nonwovens, string, twine, and braided rope.

7. The absorbent article of claim 1 wherein said first and second chambers are formed by a portion of said topsheet.

8. The absorbent article of claim 1 wherein said first and second chambers are formed by a portion of said backsheet.

9. The absorbent article of claim 1 wherein said first and second chambers are formed by a portion of said topsheet and said backsheet.

10. The absorbent article of claim 1 wherein the waist fit member is housed in a third chamber in said rear region.

11. An absorbent article comprising:
a chassis assembly having a front region, a rear region opposed to said front region, a crotch region located between said front region and said rear region, a pair of end edges, a first longitudinal edge, and a second longitudinal edge opposed to said first longitudinal edge, said chassis assembly further comprising:
  i. a topsheet,
  ii. a backsheet joined to said topsheet;
  iii. an absorbent core located between said topsheet and said backsheet;
  iv. a first ear member disposed in said rear region of said chassis assembly, said first ear member comprising a grasping region, a stretch region between said grasping region and said absorbent core, and a fastening element positioned on said grasping region;
  v. a second ear member disposed in said rear region of said chassis assembly, said second ear member comprising a second grasping region, a second stretch region between said second grasping region and said absorbent core, and a second fastening element positioned on said second grasping region;
  vi. a first chamber positioned adjacent said first longitudinal edge in said crotch region and extending from said first ear member within said grasping region to said front region;
  vii. a second chamber positioned adjacent said second longitudinal edge in said crotch region and extending from said grasping region of said second ear member to said front region;
  viii. a first substantially inelastic drawstring member extending from said first ear member to said front region through said first chamber, said first drawstring member comprising a first end secured only to said first ear member, a second end secured to said chassis assembly only in said front region, wherein said first drawstring member is not directly attached to said chassis assembly between said first end and said second end such that when said grasping region of said first ear member is pulled, said first drawstring member is put into tension to provide a more secure fit; and
  ix. a second substantially inelastic drawstring member extending from said second ear member to said front region through said second chamber, said second drawstring member comprising a first end secured only to said second ear member and a second end secured to said chassis assembly only in said front region, wherein said second drawstring member is not directly attached to said chassis assembly between said first end and said second end such that when said grasping region of said second ear member is pulled, said second drawstring member is put into tension to provide a more secure fit; and a waist fit member disposed in said rear region, said waist fit member extending from said first ear member to said second ear member, said first drawstring member having a portion connected to and overlapping with said waist fit member in the rear region, and said second drawstring member having a portion connected to and overlapping with said waist fit member in the rear region such that when said grasping portion of said first ear member is pulled, said waist fit member is put into tension to provide a more secure fit.

12. An absorbent article comprising:
a chassis assembly having a front region, a rear region opposed to said front region, a crotch region located between said front region and said rear region, a pair of end edges, a first longitudinal edge, and a second longitudinal edge opposed to said first longitudinal edge, said chassis assembly further comprising:
  i. a topsheet,
  ii. a backsheet joined to said topsheet;
  iii. an absorbent core located between said topsheet and said backsheet;
  iv. a first ear member disposed in said rear region of said chassis assembly, said first ear member comprising a grasping region, a stretch region between said grasping region and said absorbent core, and a fastening element positioned on said grasping region;
  v. a second ear member disposed in said rear region of said chassis assembly, said second ear member comprising a second grasping region, a second stretch region between said second grasping region and said absorbent core, and a second fastening element positioned on said second grasping region;
  vi. a first chamber positioned adjacent said first longitudinal edge in said crotch region and extending from said first ear member within said grasping region to said front region;
  vii. a second chamber positioned adjacent said second longitudinal edge in said crotch region and extending from said grasping region of said second ear member to said front region;

viii. a first substantially inelastic drawstring member extending from said first ear member to said front region through said first chamber, said first drawstring member comprising a first end secured to said first ear member, a second end secured to said chassis assembly in said front region, said first drawstring member being unattached to said chassis assembly between said first end and said second end such that when said grasping region of said first ear member is pulled, said first drawstring member is put into tension to provide a more secure fit; and ix. a second substantially inelastic drawstring member extending from said second ear member to said front region through said second chamber, said second drawstring member comprising a first end secured to said second ear member and a second end secured to said chassis assembly in said front region, said second drawstring member being unattached to said chassis assembly between said first end and said second end such that when said grasping region of said second ear member is pulled, said second drawstring member is put into tension to provide a more secure fit; and a waist fit member disposed in said rear region, said waist fit member extending from said first ear member to said second ear member, said first drawstring member having a portion overlapping with and directly fastened to said waist fit member in the rear region, and said second drawstring member having a portion overlapping with and directly fastened to said waist fit member in the rear region such that when said grasping portion of said first car member is pulled, said waist fit member is put into tension to provide a more secure fit.

* * * * *

UNITED STATES PATENT AND TRADEMARK OFFICE
CERTIFICATE OF CORRECTION

PATENT NO. : 7,575,573 B1  Page 1 of 1
APPLICATION NO. : 08/777849
DATED : August 18, 2009
INVENTOR(S) : Donald C. Roe et al.

It is certified that error appears in the above-identified patent and that said Letters Patent is hereby corrected as shown below:

Col. 16, Claim 1

Line 33, delete "car" and insert -- ear --.

Line 44, delete "car" and insert -- ear --.

Col. 20, Claim 12

Line 14, delete "car" and insert -- ear --.

Signed and Sealed this

Third Day of August, 2010

David J. Kappos
*Director of the United States Patent and Trademark Office*